(12) United States Patent
Yaguchi

(10) Patent No.: US 7,481,976 B2
(45) Date of Patent: Jan. 27, 2009

(54) BODY FLUID COMPONENT ANALYZING SYSTEM

(75) Inventor: Yoshiaki Yaguchi, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 526 days.

(21) Appl. No.: 10/543,498

(22) PCT Filed: Jan. 23, 2004

(86) PCT No.: PCT/JP2004/000580

§ 371 (c)(1),
(2), (4) Date: Jul. 27, 2005

(87) PCT Pub. No.: WO2004/068128

PCT Pub. Date: Aug. 12, 2004

(65) Prior Publication Data

US 2006/0151342 A1     Jul. 13, 2006

(30) Foreign Application Priority Data

Jan. 27, 2003   (JP)   ............................. 2003-016997

(51) Int. Cl.
    *G01N 21/00*   (2006.01)
(52) U.S. Cl. .................................................. 422/58
(58) Field of Classification Search .................... 422/58
    See application file for complete search history.

(56) References Cited

U.S. PATENT DOCUMENTS

| 4,935,346 | A |   | 6/1990  | Phillips et al. |
| 5,384,028 | A |   | 1/1995  | Ito |
| 5,463,467 | A |   | 10/1995 | Baumann et al. |
| 5,505,308 | A |   | 4/1996  | Eikmeier et al. |
| 5,538,688 | A |   | 7/1996  | Tezuka et al. |
| 5,720,924 | A |   | 2/1998  | Eikmeier et al. |
| 5,736,103 | A | * | 4/1998  | Pugh .......................... 422/68.1 |
| 5,872,713 | A | * | 2/1999  | Douglas et al. ............... 702/85 |
| 6,561,978 | B1 | * | 5/2003 | Conn et al. .................. 600/309 |
| 6,602,469 | B1 | * | 8/2003 | Maus et al. ................. 422/68.1 |

FOREIGN PATENT DOCUMENTS

| EP | 0 127 958    | 12/1984 |
| EP | 0 875 754 A1 | 11/1998 |
| JP | 60-17344     | 1/1985  |
| JP | 63-101757    | 5/1988  |
| JP | 7-167786     | 7/1995  |
| JP | 7-209242     | 8/1995  |
| JP | 8-502590     | 3/1996  |

(Continued)

*Primary Examiner*—Walter D Griffin
*Assistant Examiner*—Bobby Ramdhanie
(74) *Attorney, Agent, or Firm*—Buchanan Ingersoll & Rooney PC

(57) ABSTRACT

A body fluid component analyzing system in which even if the lot of sensor chips is changed, parameters can be calibrated without changing memory keys. The system comprises a measurement instrument body having calculating means for calculating a characteristic of a component, a container containing a sensor chip for sensing a characteristic of at least one component of a body fluid, and a case in which the measurement instrument body and the container are set. The calculation parameter(s) of one or more sensor chips can be automatically transferred to the measurement instrument body by transfer means.

24 Claims, 10 Drawing Sheets

FOREIGN PATENT DOCUMENTS

| | | |
|---|---|---|
| JP | 8-114603 | 5/1996 |
| JP | 9-250998 | 9/1997 |
| JP | 11-510915 | 9/1999 |
| JP | 2001-141686 | 5/2001 |
| WO | 94/29703 | 12/1994 |
| WO | 98/19159 | 7/1998 |

* cited by examiner

BODY FLUID COMPONENT ANALYZING SYSTEM

TECHNICAL FIELD

The present invention relates to a body fluid component analyzing system for quantitatively or qualitatively analyzing components of a body fluid, such as glucose, hemoglobin, etc. More specifically, the present invention is concerned with a body fluid component analyzing system including a measuring instrument having processing means, which is connected to a sensor chip having a reactive member for reacting with a component of a body fluid depending on characteristics thereof, for processing the characteristics of the component, a sensor storage unit such as a sensor container or the like for storing or packaging sensor chips, and a storage case for storing the measuring instrument and the sensor storage unit.

BACKGROUND ART

Heretofore, it has been customary to pierce the skin of a finger, an arm, an ear, or the like, sample a small amount of blood through the pierced skin, and measure various components of the blood using the sampled blood. Particularly, the measurement of a blood glucose level in a diabetic patient is important for monitoring the state of the diabetic patient. It has been recommended for the patient to perform a self glucose monitoring process to monitor daily blood glucose level changes. In view of a growing number of diabetic patients in recent years, there has been a demand for measuring processes and measuring means that are simple and painless.

Blood glucose levels are often measured using the reaction of an enzyme such as glucose oxidase, glucose dehydrogenase, or the like to oxidize glucose. At present, the measurement of a blood glucose level is performed by a blood glucose measuring device according to a colorimetric process for setting in place a test paper which produces a color depending on the amount of blood glucose brought into contact therewith, supplying the test paper with the blood to cause the test paper to give a color, and optically measuring the grade of the color to quantify the blood glucose level (see, for example, Japanese Patent Laid-open No. Sho 63-101757), or an electrode process for electrically measuring a product resulting from the enzymatic reaction referred to above (see, for example, Japanese Patent Laid-open No. Sho 60-17344).

According to the above measuring processes, a dedicated skin-piercing tool, i.e., a needle-like or knife-like piercing means known as a lancet, is used to form a cut in the skin of a patient's finger or the like to allow a body fluid such as the blood to bleed, and the body fluid is transferred to a separately prepared test chip having a test paper or an electrode sensor or the like, and then measured by the blood glucose measuring device (see, for example, Japanese Patent Laid-open No. Hei 7-167786).

For correcting variations of test papers or electrode sensors which occur from production lot to production lot, there have been known a system for recording a parameter for correcting sensor performance variations in a sensor chip (see, for example, Japanese Patent Laid-open No. Hei 7-209242) and a system for using a memory key recording a parameter depending on the production lot of sensor chips and loading the memory key into a measuring device to read the parameter into the measuring device (see, for example, Japanese Translations of PCT for Patent No. Hei 8-502590 and Japanese Translations of PCT for Patent No. Hei 11-510915).

If the memory key is used, however, the memory key needs to be replaced each time a sensor chip of a different production lot is employed. Therefore, it is awkward for the user to use the memory key.

The present invention solves the problems of the above prior art. It is an object of the present invention to provide a simple body fluid component analyzing system which does not require the user to replace a memory key each time a sensor chip of a different production lot is employed.

DISCLOSURE OF INVENTION

The above object can be achieved by structures (1) through (11) of the present invention as described below.

(1) A body fluid component analyzing system according to the present invention includes a sensor chip for detecting characteristics of at least one component of a body fluid, a measuring instrument having processing means, to which the sensor chip is adapted to be connected, for processing the characteristics of the component, a sensor chip storage unit for storing or packaging at least one the sensor chip, a storage case for storing at least the measuring instrument, parameter recording means applied to or indicated on the sensor chip storage unit, for recording at least one parameter used when the processing means of the measuring instrument processes the characteristics, parameter receiving means provided in the measuring instrument, for receiving the parameter recorded by the parameter recording means, and transfer means for transferring the parameter recorded by the parameter recording means to the parameter receiving means disposed in the measuring instrument while at least the measuring instrument is being stored in the storage case.

(2) A body fluid component analyzing system according to the present invention includes a sensor chip for detecting characteristics of at least one component of a body fluid, a measuring instrument having processing means, to which the sensor chip is adapted to be connected, for processing the characteristics of the component, a sensor chip storage unit for storing or packaging at least one the sensor chip, a storage case for storing the measuring instrument and the sensor chip storage unit, parameter recording means applied to or indicated on the sensor chip storage unit, for recording at least one parameter used when the processing means of the measuring instrument processes the characteristics, parameter receiving means disposed in the measuring instrument, for receiving the parameter recorded by the parameter recording means, and transfer means disposed in the storage case, for reading and transferring the parameter recorded by the parameter recording means to the parameter receiving means disposed in the measuring instrument while the measuring instrument and the sensor chip storage unit are being stored in the storage case.

(3) The transfer means is detachably disposed in the storage case.

(4) The parameter represents calibrating information for correcting variations of the performance of the sensor chip.

(5) The transfer means transfers the parameter while the measuring instrument and the sensor chip storage unit are being positioned in the storage case.

(6) The transfer means may include an electric transfer arrangement for transferring the parameter between the parameter recording means and the parameter receiving means through electric contacts.

(7) The transfer means may include an optical transfer arrangement for optically transferring the parameter between the parameter recording means and the parameter receiving means.

(8) The parameter transferred from the parameter recording means to the parameter receiving means by the optical transfer arrangement includes optical information represented by a bar code.

(9) The transfer means may include an acoustic transfer arrangement for acoustically transferring the parameter between the parameter recording means and the parameter receiving means.

(10) The transfer means may include a radio-wave transfer arrangement for transferring the parameter between the parameter recording means and the parameter receiving means by way of a radio wave.

(11) The transfer means may include an electromagnetic transfer arrangement for electromagnetically transferring the parameter between the parameter recording means and the parameter receiving means.

When the sensor storage unit in which at least one sensor chip is stored or packaged and the measuring instrument are stored in the storage case, at least one parameter of the sensor chip is automatically transferred from the parameter recording means applied to or indicated on the sensor storage unit to the parameter receiving means of the measuring instrument by the transfer means, and the parameter of the measuring instrument is automatically calibrated. Therefore, the parameter can be calibrated without the need for loading the sensor chip into the measuring instrument each time the lot for the sensor chip is changed.

DETAILED DESCRIPTION

Embodiments of a body fluid component analyzing system according to the present invention will be described below with reference to the drawings.

Figure 1A:
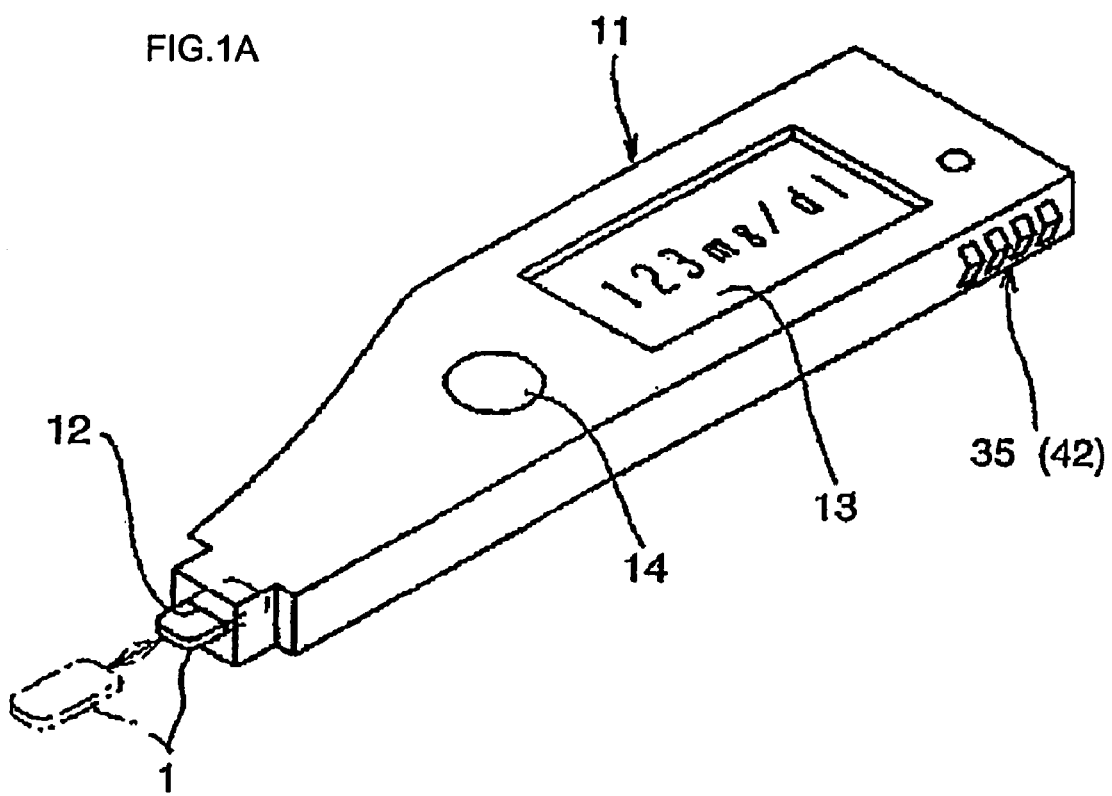
FIGS. 1A and 1B are perspective views of a measuring instrument and a sensor chip and an enlarged perspective view of the sensor chip in a body fluid component analyzing system according to an embodiment of the present invention.
Figure 1B:
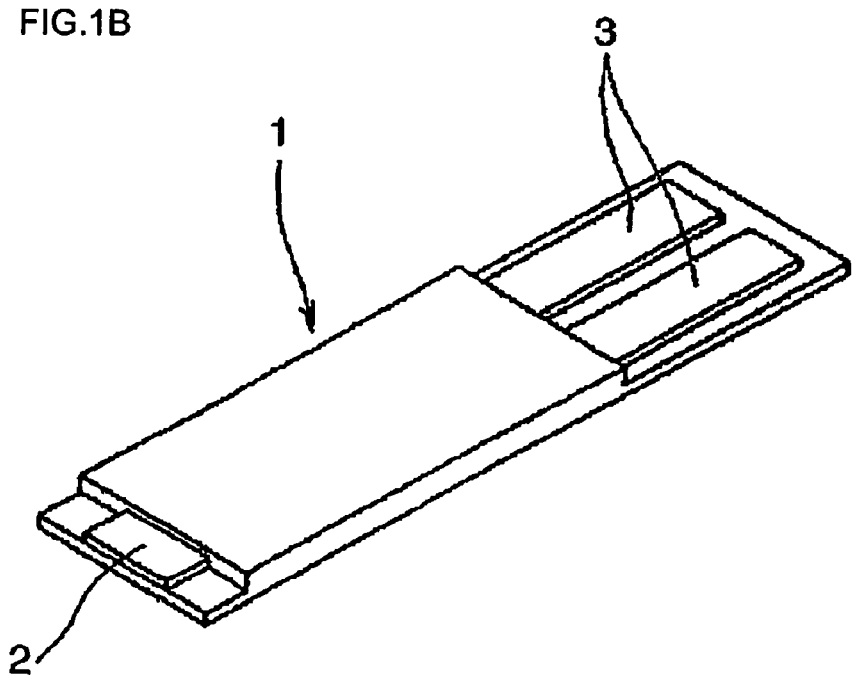

FIGS. 1A and 1B schematically show a sensor chip 1 and a measuring instrument 11 such as a blood glucose level measuring instrument or the like. The sensor chip 1 has a reactive member 2 for reacting with a component such as a blood glucose level or the like and electrode terminals 3. The measuring instrument 11 has a sensor chip mount 12 such as a slit or the like for removably mounting the sensor chip 1 therein, a component display unit 13 such as a liquid crystal panel or the like for digitally displaying a component such as a blood glucose level or the like, and a switch 14 such as a switch button or the like.

In use, the electrode terminals 3 of the sensor chip 1 are removably mounted in the sensor chip mount 12 of the measuring instrument 11.

After a finger of a hand of the patient is pierced by a piercing tool or the like to draw a body fluid such as the blood or the like therefrom, the drawn body fluid such as the blood or the like is applied as a dot or drop to the reactive member 2 of the sensor chip 1 mounted in the tip end of the measuring instrument 11. The switch 14 is turned on to digitally display the value of a component such as a blood glucose level or the like in the body fluid on the component display unit 13.

Details of the body fluid component analyzing system according to the present invention will be described below.

Figure 2:
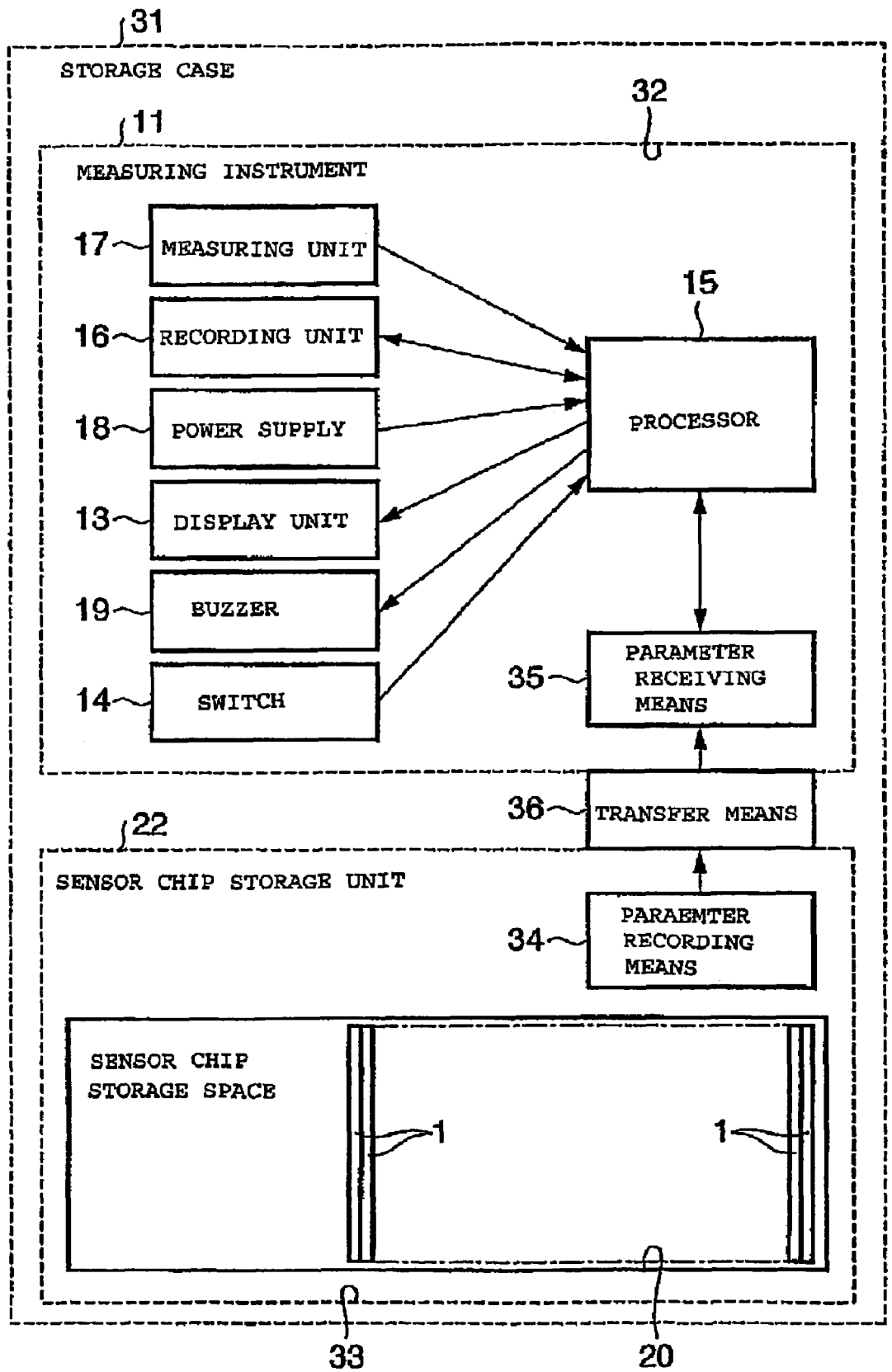
FIG. 2 is a block diagram of a body fluid component analyzing system according to an embodiment of the present invention.

FIG. 2 is a block diagram showing a general arrangement of the body fluid component analyzing system. The body fluid component analyzing system performs an automatic calibrating process automatically in a storage case 31 for correcting performance variations due to different manufacturing lots of sensor chips 1.

Figure 3A:
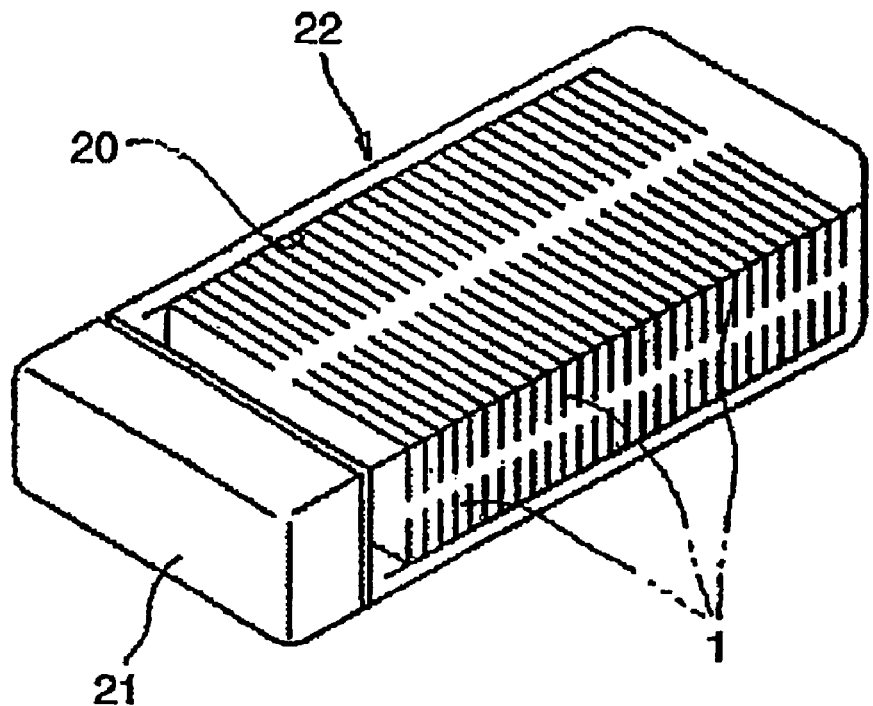
FIGS. 3A and 3B are perspective views of a sensor chip storage unit in the body fluid component analyzing system according to the embodiment of the present invention.
Figure 3B:
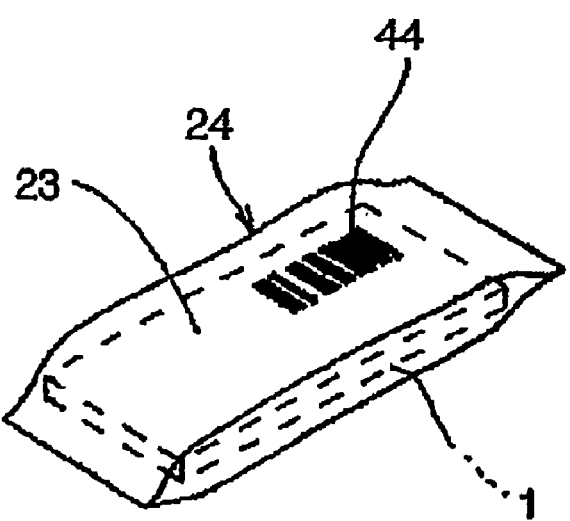

FIG. 3A shows a sensor chip storage unit 22 which is a container with an openable/closable lid 21 for storing a number of (e.g., 20 to 50) sensor chips 1 of one production lot in a sensor chip storage space 20 formed as an inner space. FIG. 3B shows a sensor chip storage unit 24 having a small number of (one to several) sensor chips 1 packaged in a package 23. A bar code 44 is used to acquire parameters with an optical parameter transmission arrangement described later on.

The body fluid component analyzing system shown in FIG. 2 may be implemented with either one of the two sensor chip storage units 22, 24. In this embodiment described below, the sensor chip storage unit 22 is used.

The storage case 31 has a positioning unit 32 for the measuring instrument 11 and a positioning unit 33 for the sensor chip storage unit 22. The two positioning unit 32, 33 are disposed adjacent to each other in the storage case 31. The measuring instrument 11 and the sensor chip storage unit 22 are stored and positioned respectively in the positioning units 32, 33.

A parameter recording means 34 for recording at least one parameter which represents calibrating information (a calibrating coefficient for sensor output, etc.) for correcting variations of the performance of the sensor chips 1 stored in the sensor chip storage unit 22 is applied to or indicated on one of the side faces of the sensor chip storage unit 22. A parameter receiving means 35 is applied to a confronting side face of the measuring instrument 11. The parameter stored in the parameter recording means is common among the sensor chips stored in the storage case 31. Thus, the parameter is identical in each lot.

When the measuring instrument 11 and the sensor chip storage unit 22 are inserted and positioned respectively in the positioning units 32, 33, the parameter recording means 34 and the parameter receiving means 35 are brought into contact with each other or closely to each other.

A transfer means 36 then automatically transfers the at least one parameter of the sensor chips 1 from the parameter recording means 34 of the sensor chip storage unit 22 to the parameter receiving means 35 of the measuring instrument 11, and the transferred parameter is input to a processor 15. The processor 15 automatically corrects a performance variation of the sensor chips 1 due to a production lot difference or the like, and stores the corrected performance variation into a memory 16. As shown in FIG. 2, the measuring instrument 11 comprises, in addition to other features, a measuring unit 17, a power supply 18, and a buzzer 19 serving as alarm means. For measuring a component of a body fluid such as a blood glucose level as described above, the switch 14 is turned on to enable the processor 15 to process characteristics of a component of a body fluid that is measured by the measuring unit 17, store the processed characteristics in the memory 16, and digitally display the processed characteristics on the display unit 13. If a measurement error occurs or the characteristics exceed a reference value, then the processor 15 controls the buzzer 19 to give an alarm.

Specific examples of the body fluid component analyzing system according to the present invention will be described below with reference to FIGS. 4-8.

Figure 4:
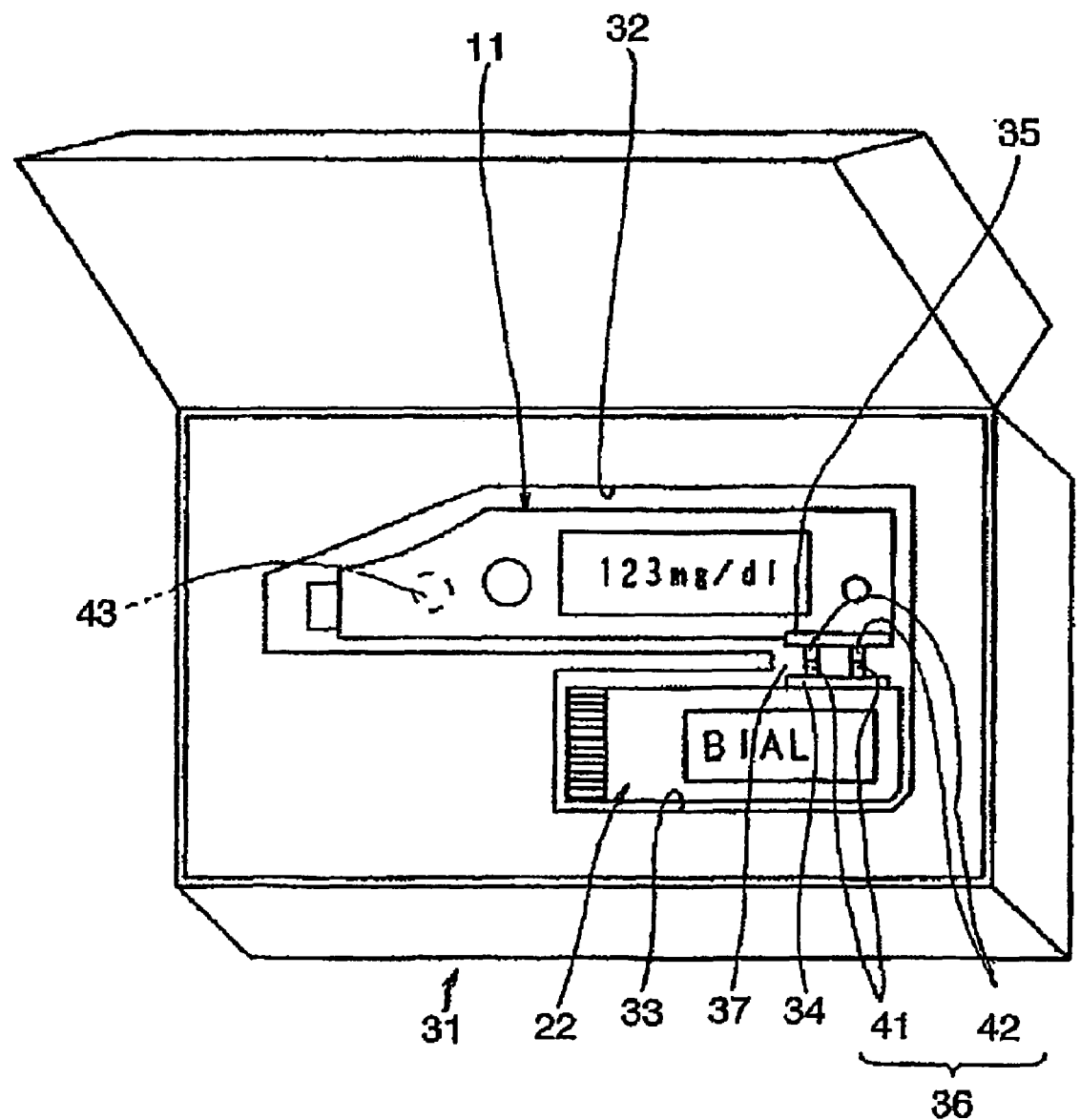
FIG. 4 is a perspective view illustrating an electric parameter transfer arrangement for use in the body fluid component analyzing system according to the present invention.

A body fluid component analyzing system shown in FIG. 4 employs an electric transfer arrangement as the transfer means 36. The parameter recording means 34 of the sensor chip storage unit 22 and the parameter receiving means 35 of the measuring instrument 11 include at least a pair of electric contacts 41, 42. The positioning units 32, 33, which are cut out along the profiles of the measuring instrument 11 and the sensor chip storage unit 22 respectively are disposed adjacent to each other in the storage case 31. An insertion unit 37 for inserting the transfer means 36 therein is formed as a recess in the region across which the positioning units 32, 33 are disposed adjacent to each other. A detection switch 43 is disposed on the bottom of the positioning unit 32, for example. The detection switch 43 serves as a switch for detecting when the measuring instrument 11 is placed in the storage case 31. The detection switch 43 may be any switch such as a mechanical switch, an electrical switch, or the like insofar as it can detect when the measuring instrument 11 is placed in the storage case 31.

When the measuring instrument 11 and the sensor chip storage unit 22 are properly set (inserted and positioned) in the respective positioning units 32, 33 in the storage case 31, the electric contacts 441, 42 are brought into contact with each other in the insertion unit 37. The detection switch 43 detects when the measuring instrument 11 is set in the positioning unit 32, for example. Then, the process of automatically transferring the parameter from the sensor chip storage unit 22 to the measuring instrument 11 is performed. The automatic parameter transfer process is performed successively at certain time intervals (e.g., in every hour). According to the present invention, simply when the measuring instrument 11 and the sensor chip storage unit 22 are mounted in the storage case 31, the parameter is thereafter automatically periodically transferred from the sensor chip 22 to the measuring instrument 11. Consequently, as the parameter is calibrated without troubling the user (while the user is unconscious), the body fluid component analyzing system is convenient to use. Once the parameter calibrating process is performed, the automatic parameter transfer may be stopped until the measuring instrument 11 and/or the sensor chip storage unit 22 is removed (the detection switch 43 also detects when the measuring instrument 11 and/or the sensor chip storage unit 22 is removed), thereby simplifying the entire process.

Figure 5:
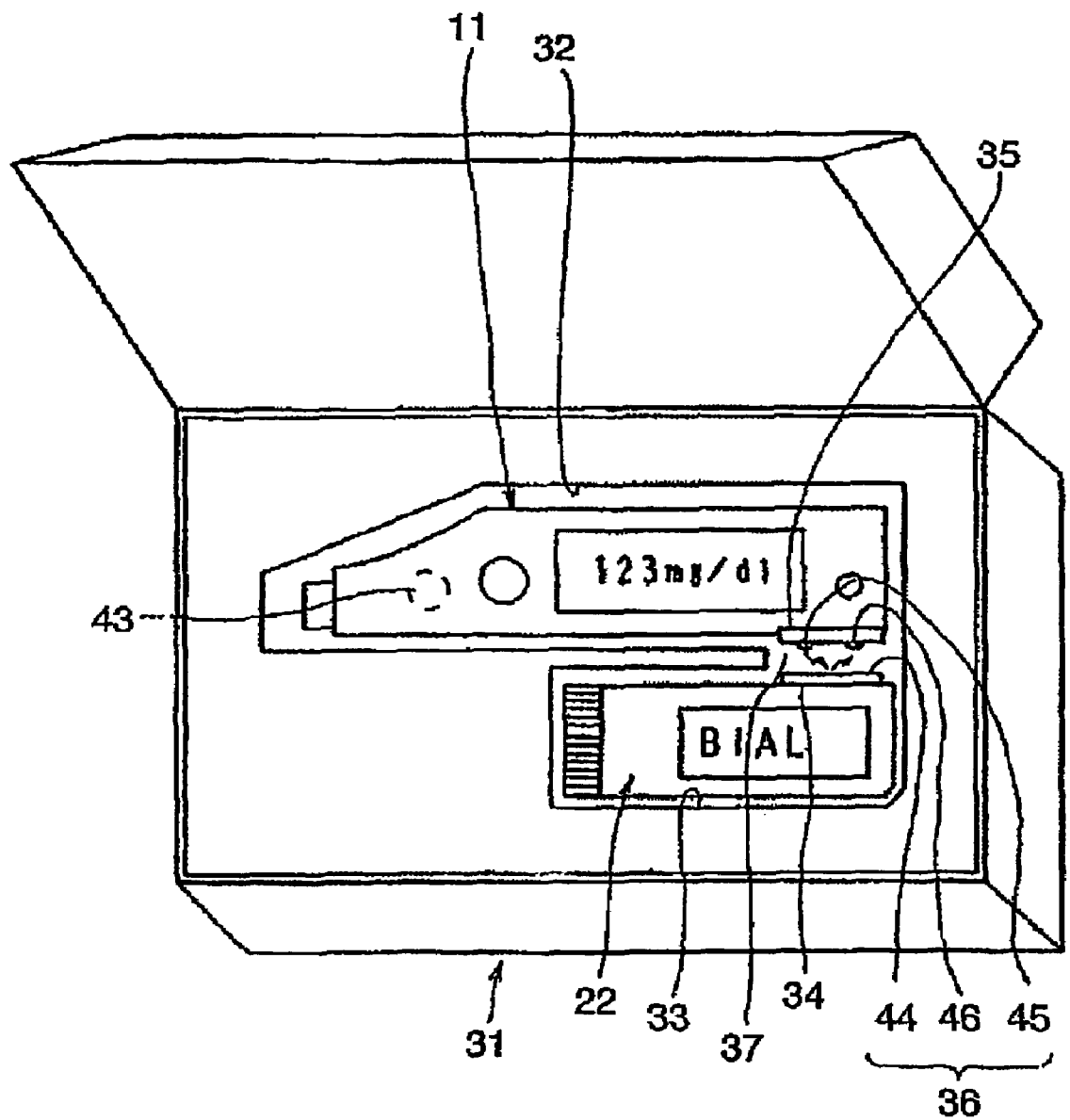
FIG. 5 is a perspective view illustrating an optical parameter transfer arrangement for use in the body fluid component analyzing system according to the present invention.

FIG. 5 shows a body fluid component analyzing system wherein an optical transfer arrangement is employed as the transfer means 36. The parameter recording means 34 of the sensor chip storage unit 22 includes optically readable indicating means such as the bar code 44 (see FIG. 3B) or the like. The parameter receiving means 35 of the measuring instrument 11 is constructed as light-reflecting reading means including a light-emitting element 45 such as an LED or the like and a light-detecting element 46 such as a phototransistor or the like.

When the measuring instrument 11 and the sensor chip storage unit 22 are properly set in the respective positioning units 32, 33 in the storage case 31, the bar code 44 is illuminated by the light-emitting element 45 across the insertion unit 37, and reflects light which is detected by the light-detecting element 46. The parameter represented by the bar code 44 is automatically transferred from the sensor chip storage unit 22 to the measuring instrument 11 as described above.

Since the bar code 44 can be used by the optical transfer arrangement, it is sufficiently possible to employ the sensor chip storage unit 24 which has the small number of (one to several) sensor chips 1 packaged in the package 23, as shown in FIG. 3B, as the sensor chip storage unit.

Figure 6:
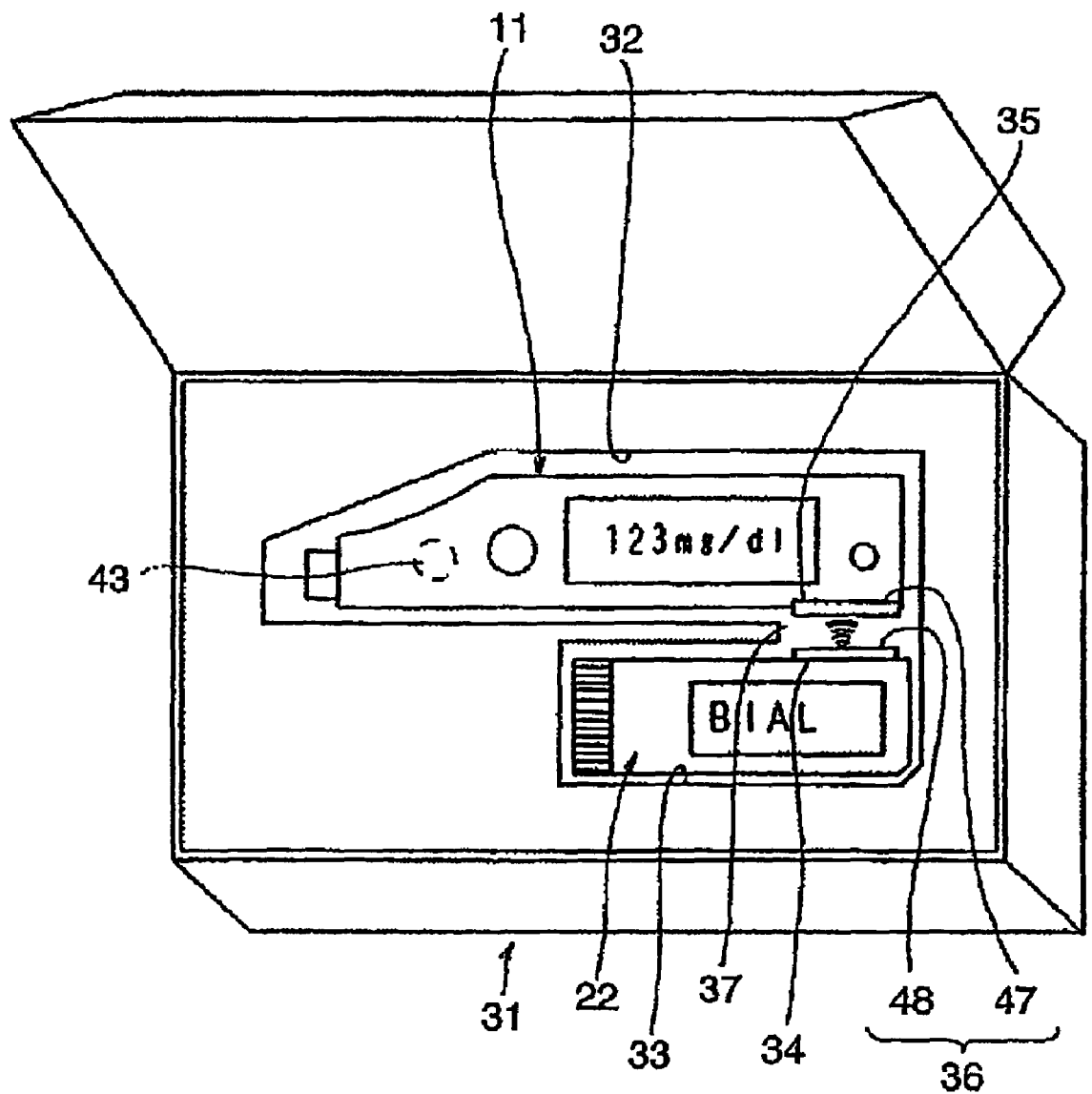
FIG. 6 is a perspective view illustrating an acoustic parameter transfer arrangement for use in the body fluid component analyzing system according to the present invention.

FIG. 6 shows a body fluid component analyzing system wherein an acoustic transfer arrangement is employed as the transfer means 36. The parameter recording means 34 of the sensor chip storage unit 22 includes an acoustic oscillating means 47 which oscillates acoustically. The parameter receiving means 35 of the measuring instrument 11 is constructed as an acoustic transmitting and receiving means (e.g., means using a high-frequency wave such as a telephonic pulse or push-tone wave) 48 for transmitting and receiving acoustic energy.

When the measuring instrument 11 and the sensor chip storage unit 22 are properly set in the respective positioning units 32, 33 in the storage case 31, the acoustic transmitting and receiving means 48 oscillates a high-frequency wave, and the acoustic oscillating means 47 is vibrated thereby across the insertion unit 37, whereupon the parameter is automatically transferred from the sensor chip storage unit 22 to the measuring instrument 11 in the same manner as described above.

Figure 7:
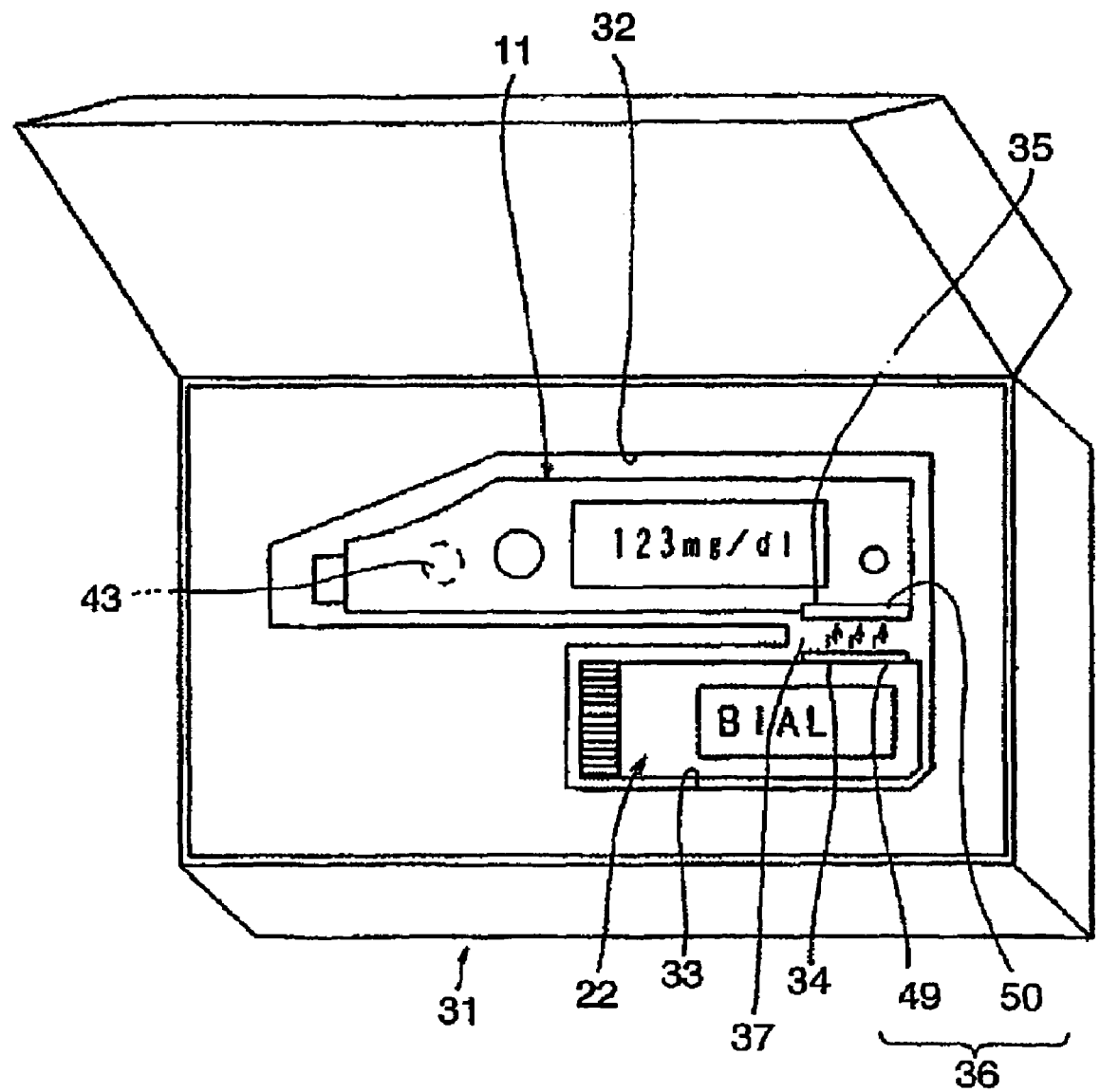
FIG. 7 is a perspective view illustrating a radio-wave parameter transfer arrangement for use in the body fluid component analyzing system according to the present invention.

FIG. 7 shows a body fluid component analyzing system wherein a radio-wave transfer arrangement is employed as the transfer means 36. The parameter recording means 34 of the sensor chip storage unit 22 includes a radio-wave transmitting means 49, and the parameter receiving means 35 of the measuring instrument 11 is constructed as a radio-wave transmitting and receiving means 50.

When the measuring instrument 11 and the sensor chip storage unit 22 are properly set in the respective positioning units 32, 33 in the storage case 31, the radio-wave transmitting and receiving means 49 sends radio-wave information to the radio-wave transmitting and receiving means 50 across the insertion unit 37 due to the reflection of a radio wave transmitted from the radio-wave transmitting and receiving means 50, whereupon the parameter is automatically transferred from the sensor chip storage unit 22 to the measuring instrument 11 in the same manner as described above.

Figure 8:
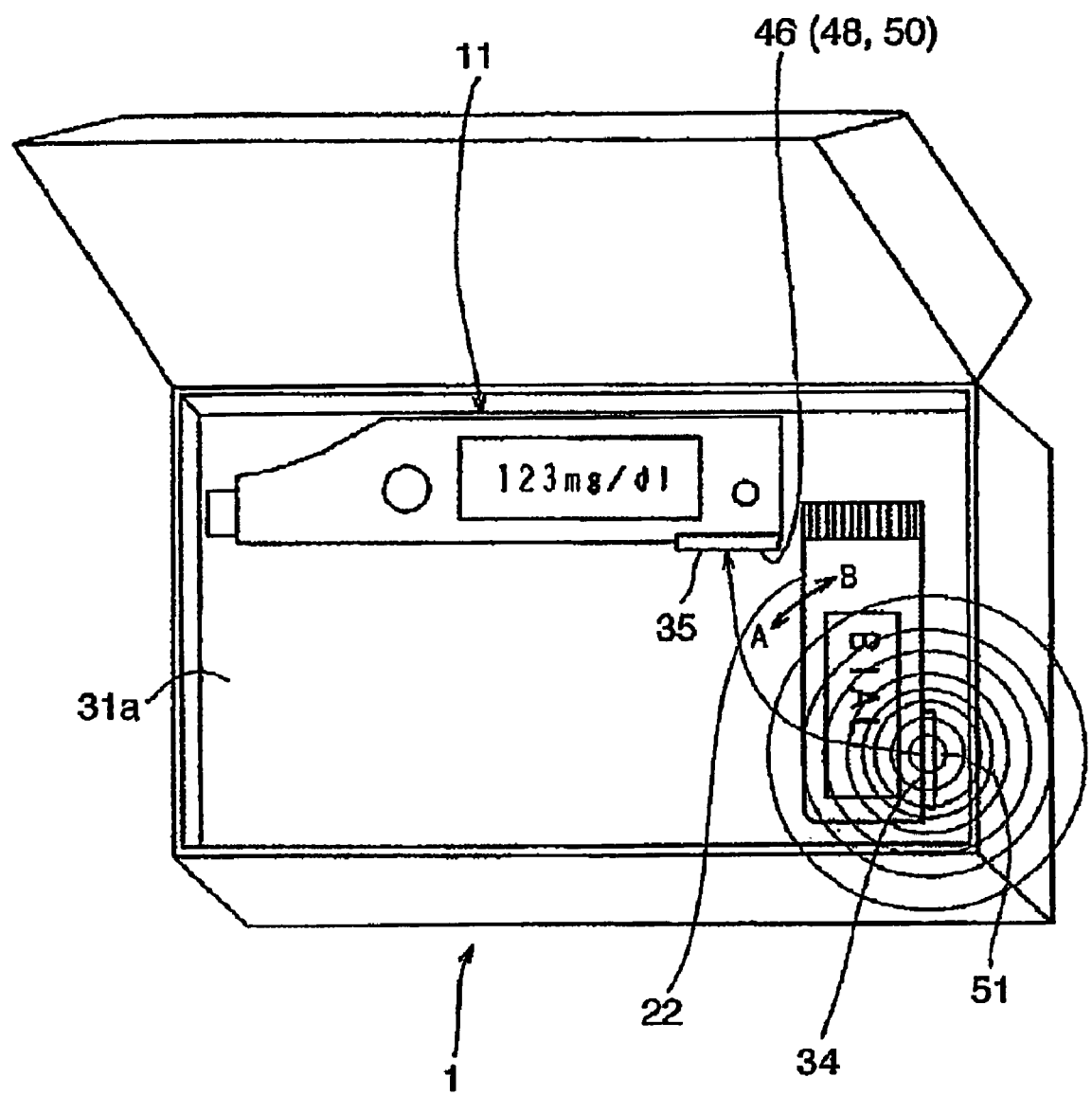
FIG. 8 is a perspective view illustrating a contactless parameter transfer arrangement for use in the body fluid component analyzing system according to the present invention.

FIG. 8 shows a body fluid component analyzing system wherein a contactless proximity transfer arrangement is employed as the transfer means 36. A storage region 31a which is widely open in the storage case 31 has no positioning units disposed therein for the measuring instrument 11 and the sensor chip storage unit 22. Therefore, the measuring instrument 11 and the sensor chip storage unit 22 are housed in the storage region 31a without being positionally limited. A contactless transfer means 51 such as the radio-wave (electromagnetic) transfer arrangement, the acoustic transfer arrangement, or the like as described above is disposed on the bottom of the storage region 31a. When the sensor chip storage unit 22 approaches the contactless transfer means 51, the parameter of the parameter recording means 34 is read by the contactless transfer means 51, and automatically transferred to the parameter receiving means 35 of the measuring instrument 11. With this structure, the measuring instrument 11 and the sensor chip storage unit 22 are not required to be positioned at particular places, but may be moved within the storage case 31, as indicated by the arrows A, B. However, since both the measuring instrument 11 and the sensor chip storage unit 22 as they are placed in the storage case 31 have to be detected by something like the detection switch 43, if the detection switch 43 includes a contact-type switch, then it is desirable that either one of the measuring instrument 11 and the sensor chip storage unit 22 be disposed for contact with the detection switch 43.

Figure 9:
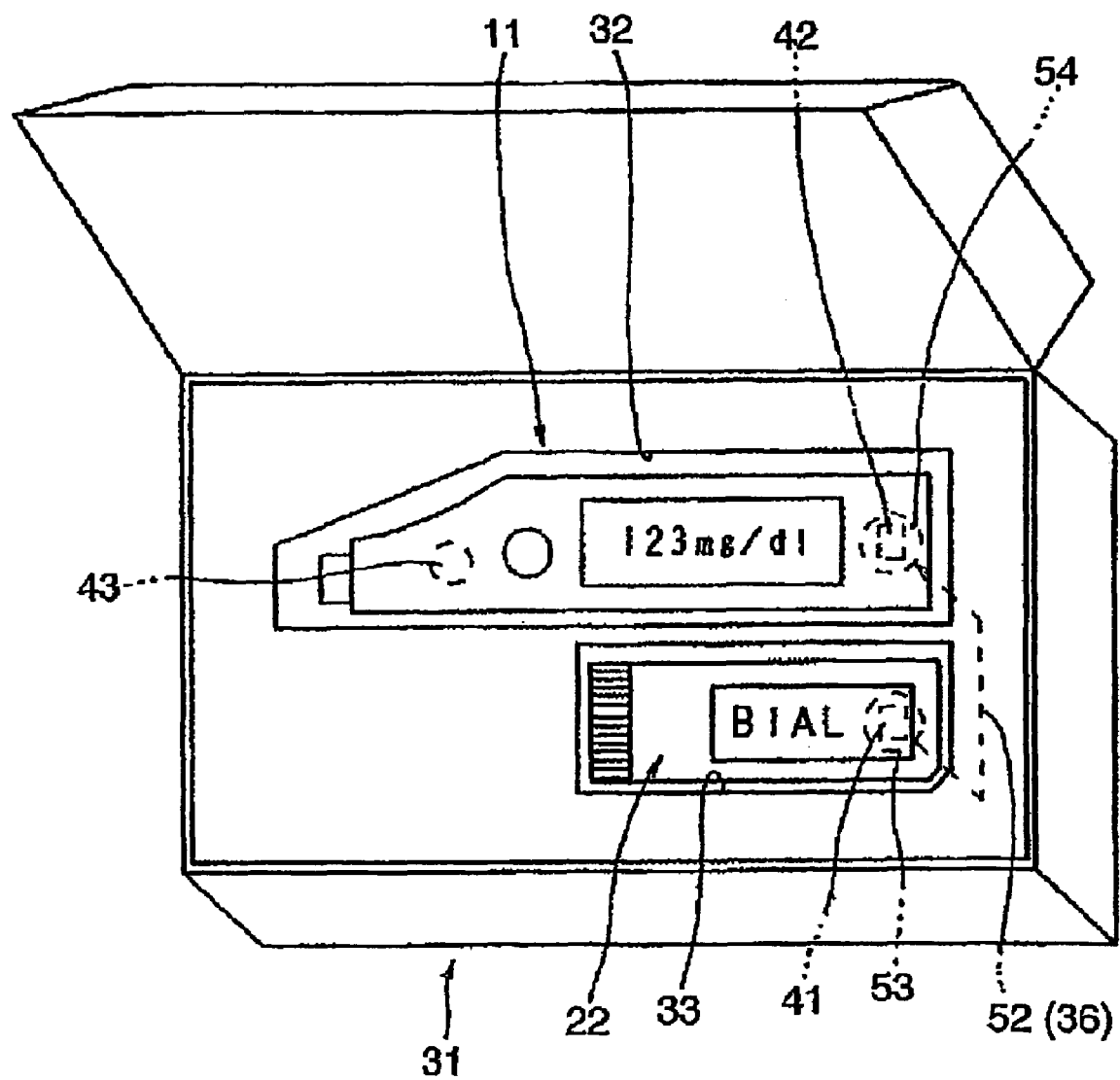
FIG. 9 is a perspective view illustrating a parameter transfer arrangement using, as a medium, a storage case of the body fluid component analyzing system according to the present invention.

FIG. 9 shows a body fluid component analyzing system wherein an indirect transfer arrangement is employed which uses the storage case 31 as a medium. A transmitter 53 and a receiver 54 of an indirect transfer means 52 such as the electric transfer arrangement, the optical transfer arrangement, the acoustic transfer arrangement, the radio-wave (electromagnetic) transfer arrangement, or the like as described above are disposed on the bottoms of the positioning units 32, 33 of the measuring instrument 11 and the sensor chip storage unit22 in the storage case 31. When the measuring instrument11 and the sensor chip storage unit 22 are set in the respective positioning units 32, 33, the parameter recording means 41 and the parameter receiving means 42 disposed on the bottoms of the sensor chip storage unit 22 and the measuring instrument 11 contact or approach the transmitter 53 and the receiver 54 of the indirect transfer means 52. The parameter of the parameter recording means 41 of the sensor chip storage unit 22 is read by the transmitter 53, and transferred by the indirect transfer means 52 to the parameter receiving means 42 of the measuring instrument 11 through the receiver 54.

Figure 10:
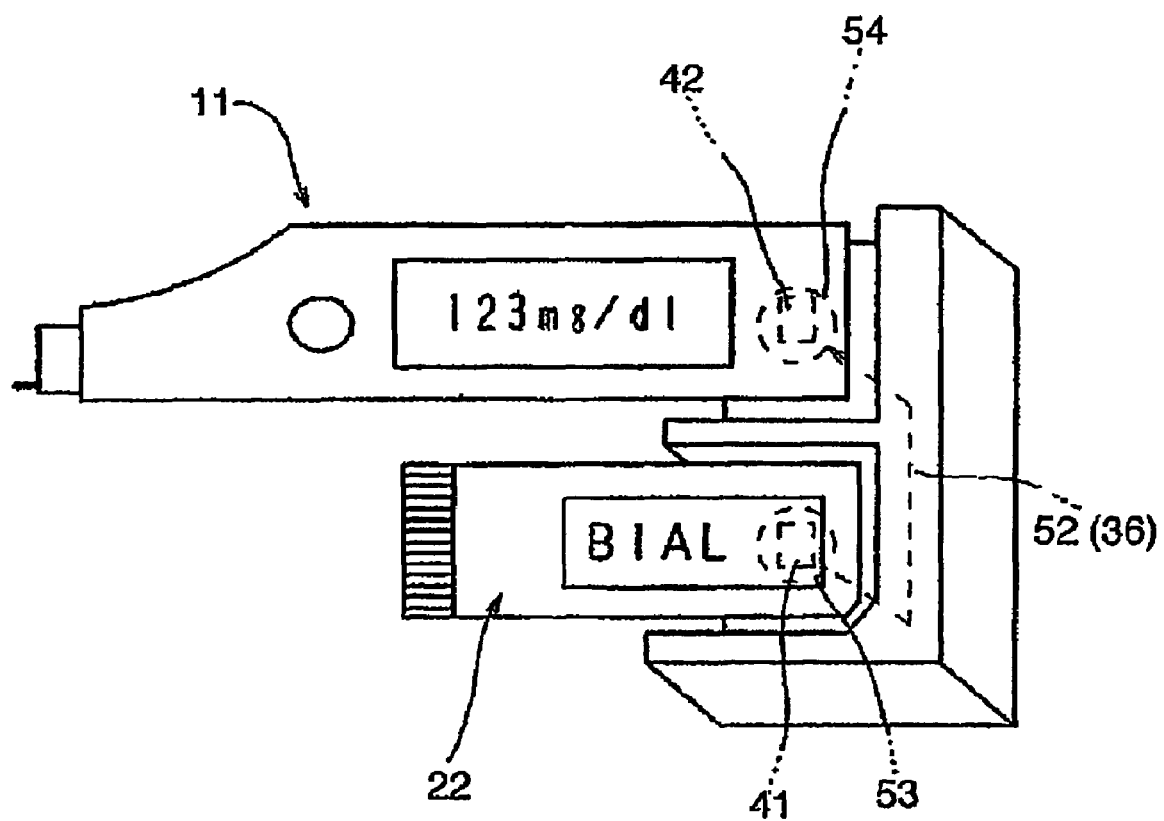
FIG. 10 is a perspective view illustrating the parameter transfer arrangement using, as a medium, the storage case of the body fluid component analyzing system according to the present invention, with a transfer function section being detachable.

FIG. 10 shows a transfer function section detached from the indirect transfer arrangement according to the embodiment shown in FIG. 9. The transfer means of the indirect transfer arrangement is detachable from the storage case. This structure allows the parameter to be calibrated outside of the storage case.

Although the embodiments of the present invention has been described above, the present invention is not limited to the above embodiments, but various changes and modifications may be made therein based on the technical concept of the present invention.

For example, in the above embodiments, both the measuring instrument 11 and the sensor chip storage unit are stored in the storage case 31 for automatically transferring the parameter. However, only the measuring instrument 11 may be stored (set) in the storage case, and the sensor chip storage unit 22 may be brought close to the storage case to automatically transfer the parameter from the sensor chip storage unit 22 to the measuring instrument 11.

Since the body fluid component analyzing system thus constructed according to the present invention is capable of automatically transferring the parameter from the sensor chip to the measuring instrument, the parameter can automatically be calibrated when the lot for the parameter is changed without the need for the user to replace a memory key or to load the parameter into the measuring instrument each time the lot for the parameter is changed.

When the lot of the sensor chip which is a consumable product requiring calibration at present is changed, information that is required for calibrating the parameter can reliably be input to the measuring instrument while the user is unconscious, so that the measuring accuracy of the measuring instrument is maintained. Therefore, the diabetic patient can measure a blood glucose level at ease.

Since the user is not required to be conscious, the user can use the body fluid component analyzing system in substantially the same manner as when no parameter is calibrated, so that the diabetic patient is less troubled by the use of the system.

In the embodiment which applies the optical measurement, only a bar code or another code may be placed on the sensor chip storage unit, and hence the expenses of the sensor chip which is a consumable product are not increased. As no special device needs to be added to the storage case, the expenses of the storage case are not increased.

The invention claimed is:

1. A body fluid component analyzing system comprising:
a sensor chip for detecting characteristics of at least one component of a body fluid;
a measuring instrument comprising processing means, to which said sensor chip is adapted to be connected, for processing the characteristics of said component;
a sensor chip storage unit for storing or packaging said sensor chip;
a storage case for storing at least said measuring instrument;
said sensor chip storage unit comprising parameter recording means for recording at least one parameter used when said processing means of said measuring instrument processes the characteristics;
said measuring instrument comprising parameter receiving means for receiving said at least one parameter recorded at said parameter recording means of said sensor chip storage unit; and
transfer means for transferring said at least one parameter recorded at said parameter recording means to said parameter receiving means of said measuring instrument while at least said measuring instrument is stored in said storage case.

2. A body fluid component analyzing system comprising:
a sensor chip for detecting characteristics of at least one component of a body fluid;
a measuring instrument comprising processing means, to which said sensor chip is adapted to be connected, for processing the characteristics of said component;
a sensor chip storage unit for storing or packaging said sensor chip;
a storage case for storing said measuring instrument and said sensor chip storage unit;
said sensor chip storage unit comprising parameter recording means for recording at least one parameter used when said processing means of said measuring instrument processes the characteristics;

said measuring instrument comprising parameter receiving means for receiving said at least one parameter recorded by said parameter recording means of said sensor chip storage unit; and transfer means disposed in said storage case, for reading and transferring said at least one parameter recorded by said parameter recording means to said parameter receiving means of said measuring instrument while said measuring instrument and said sensor chip storage unit are stored in said storage case.

3. A body fluid component analyzing system according to claim 2, wherein said transfer means is detachably disposed in said storage case.

4. A body fluid component analyzing system according to claim 1, wherein said at least one parameter represents calibrating information for correcting variations of the performance of said sensor chip.

5. A body fluid component analyzing system according to claim 1, wherein said transfer means transfers said at least one parameter while said measuring instrument and said sensor chip storage unit are positioned in said storage case.

6. A body fluid component analyzing system according to claim 1, wherein said transfer means comprises an electric transfer arrangement for transferring said at least one parameter between said parameter recording means and said parameter receiving means through electric contacts.

7. A body fluid component analyzing system according to claim 1, wherein said transfer means comprises an optical transfer arrangement for optically transferring said at least one parameter between said parameter recording means and said parameter receiving means.

8. A body fluid component analyzing system according to claim 1, wherein said transfer means comprises an acoustic transfer arrangement for acoustically transferring said at least one parameter between said parameter recording means and said parameter receiving means.

9. A body fluid component analyzing system according to claim 1, wherein said transfer means comprises a radio-wave transfer arrangement for transferring said at least one parameter between said parameter recording means and said parameter receiving means by way of a radio wave.

10. A body fluid component analyzing system according to claim 1, wherein said transfer means comprises an electromagnetic transfer arrangement for electromagnetically transferring said at least one parameter between said parameter recording means and said parameter receiving means.

11. A body fluid component analyzing system according to claim 1, wherein said transfer means is detachably disposed in said storage case.

12. A body fluid component analyzing system according to claim 2, wherein said at least one parameter represents calibrating information for correcting variations of the performance of said sensor chip.

13. A body fluid component analyzing system according to claim 2, wherein said transfer means transfers said at least one parameter while said measuring instrument and said sensor chip storage unit are positioned in said storage case.

14. A body fluid component analyzing system according to claim 2, wherein said transfer means comprises an electric transfer arrangement for transferring said at least one parameter between said parameter recording means and said parameter receiving means through electric contacts.

15. A body fluid component analyzing system according to claim 2, wherein said transfer means comprises an optical transfer arrangement for optically transferring said at least one parameter between said parameter recording means and said parameter receiving means.

16. A body fluid component analyzing system according to claim 2, wherein said transfer means comprises an acoustic transfer arrangement for acoustically transferring said at least one parameter between said parameter recording means and said parameter receiving means.

17. A body fluid component analyzing system according to claim 2, wherein said transfer means comprises a radio-wave transfer arrangement for transferring said at least one parameter between said parameter recording means and said parameter receiving means by way of a radio wave.

18. A body fluid component analyzing system according to claim 2, wherein said transfer means comprises an electromagnetic transfer arrangement for electromagnetically transferring said at least one parameter between said parameter recording means and said parameter receiving means.

19. A method comprising positioning a measuring instrument and a sensor chip storage unit relative to one another to permit transfer of at least one parameter from the sensor chip storage unit to the measuring instrument, with a sensor chip which detects characteristics of at least one component of a body fluid being positioned in the sensor chip storage unit and being adapted to be mounted on the measuring instrument, and the measuring instrument comprising processing means to which said sensor chip is connected, when said sensor chip is mounted on the measuring instrument, for processing the characteristics of the component;

transferring the at least one parameter from the sensor chip storage unit to the measuring instrument; and using the at least one parameter transferred from the sensor chip storage unit to the measuring instrument when processing the characteristics of the at least one component of the body fluid after said sensor chip is mounted on the measuring instrument.

20. A method according to claim 19, wherein said at least one parameter is transferred from parameter recording means for recording said at least one parameter, said parameter recording means being provided at said sensor chip storage unit.

21. A method according to claim 20, wherein said at least one parameter is transferred to parameter receiving means for receiving said at least one parameter recorded at said parameter recording means, said parameter receiving means being provided at said measuring instrument.

22. A method according to claim 19, wherein said at least one parameter is transferred to parameter receiving means for receiving said at least one parameter, said parameter receiving means being provided at said measuring instrument.

23. A method according to claim 19, further comprising positioning the measuring instrument in a storage case before transferring the at least one parameter from the sensor chip storage unit to the measuring instrument.

24. A method according to claim 23, further comprising positioning the sensor chip storage unit in the storage case before transferring the at least one parameter from the sensor chip storage unit to the measuring instrument.

* * * * *